United States Patent [19]

Wells et al.

[11] Patent Number: 4,521,600

[45] Date of Patent: Jun. 4, 1985

[54] TRIETHYLENEDIAMINE PREPARATION VIA PHOSPHATE CATALYSTS

[75] Inventors: James E. Wells, Ardmore; Victoria Eskinazi, Boothwyn, both of Pa.

[73] Assignee: Air Products and Chemicals, Inc., Allentown, Pa.

[21] Appl. No.: 381,232

[22] Filed: May 24, 1982

[51] Int. Cl.$^3$ .............................................. C07D 487/08
[52] U.S. Cl. .................................................. 544/352
[58] Field of Search ......................................... 544/352

[56] References Cited

U.S. PATENT DOCUMENTS 3,342,820  9/1967  Brader .................................. 544/352

OTHER PUBLICATIONS

Richard A. Nyquist & Ronald O. Kagel, Infrared Spectra of Inorganic Compounds, 1971, p. 163.

Primary Examiner—Robert W. Ramsuer
Attorney, Agent, or Firm—Russell L. Brewer; Richard A. Dannells, Jr.; E. Eugene Innis

[57] ABSTRACT

Certain hydrogen phosphate and pyrophosphate compositions are employed as catalysts for organic condensation reactions. Particularly high conversions and selectivities are obtained by the use of synergistic mixtures of in cyclization reactions such as in the conversion of hydroxyethylpiperazine to triethylenediamine and morpholine to dimethylaminoethylmorpholine.

8 Claims, No Drawings

TRIETHYLENEDIAMINE PREPARATION VIA PHOSPHATE CATALYSTS

TECHNICAL FIELD OF THE INVENTION

The present invention relates to organic condensation reactions effected in the presence of novel pyrophosphate and hydrogen phosphate catalysts and is more particularly concerned with the production of amine compounds in enhanced yields.

BACKGROUND OF THE PRIOR ART

Organic synthesis by condensation reactions resulting in the loss of a molecule of water or of ammonia are well known in the art. Certain of such reactions are generally effected in the presence of acidic catalysts. An important area in which such acid catalysis has been employed is in cyclization reactions as in the synthesis of triethylenediamine and its C-substituted homologues. The catalysts more generally used or proposed for use in such cyclization reactions are solid products of the Lewis acid type.

Triethylenediamine, also called diazabicyclo-[2.2.2]-octane, has been widely employed commercially as a catalyst in organic isocyanate reactions with compounds containing labile hydrogen, as in the production of urethane polymers. Triethylenediamine (sometimes hereinafter referred to as TEDA) was initially prepared in significant quantities by methods such as that described in U.S. Pat. No. 2,937,176, by passing aliphatic amines in vapor phase over acidic cracking catalyst, such as silica-alumina dried gel or acid-activated clays. Numerous other feed stocks as well as other catalysts are disclosed in subsequent patents for preparation of TEDA as well as C-alkyl derivatives thereof.

Typical among these are U.S. Pat. Nos. 2,985,658 and 3,166,558 employing preferably silica-alumina type catalyst, but listing also other useful solid acid catalysts that can be employed such as alumina in which phosphate or fluoride ion is incorporated (U.S. Pat. No. 2,985,658).

Among other catalysts proposed in the patent art for preparation of triethylene diamine and/or C-alkyl homologues thereof, are certain phosphate compounds, particularly aluminum phosphate.

The use of aluminum phosphate as a catalyst in the preparation of heterocyclic compounds from aliphatic amines was early disclosed in U.S. Pat. No. 2,467,205, particularly for the preparation of piperazine from ethylenediamine or from polyethylene polyamine. The use of aluminum phosphate as catalyst in the preparation of triethylenediamine accompanied by piperazine among other by-products is further described in U.S. Pat. No. 3,172,891; while U.S. Pat. No. 3,342,820 describes the use of complex phosphates of alkali metal and trivalent metals in the preparation of C-alkyl TEDA.

U.S. Pat. No. 3,297,701 discloses as catalysts for preparation of TEDA and C-alkyl TEDA, in addition to the preferred aluminum phosphate stated to be superior, other phosphate compounds including calcium and iron phosphates among other listed metal phosphates. In the conversion of N-aminoethylpiperazine to triethylenediamine over aluminum phosphate catalyst, at most up to 39 mol% triethylenediamine is said to be obtained. Other of the named metal phosphate catalysts in the examples of the patent obtain yields of less than 10 mol% TEDA.

Acid metal phosphate catalysts, particularly phosphates of boron, aluminum and trivalent iron, have also been proposed for use in intramolecular cyclic dehydration reactions and other condensation reactions involving amino compounds. Examples of such reactions are found in U.S. Pat. No. 4,117,227, which discloses conversion of an N-substituted diethanolamine to the corresponding N-substituted morpholine. U.S. Pat. No. 4,036,881 describes preparation of non-cyclic polyalkylene polyamines by condensation of an alkylene diamine with an ethanolamine. N-hydroxyethylmorpholine is condensed with morpholine in the presence of aluminum phosphate catalyst to form dimorpholino ethane according to U.S. Pat. No. 4,103,087. Similarly, dimorpholinodiethyl ether is obtained by condensation of hydroxyethyl morpholine with aminoethyl morpholine over iron, aluminum or boron phosphate in U.S. Pat. No. 4,095,022. Reaction of piperazine with ethanolamine over such acidic metal phosphate produces N-aminoethyl piperazine according to U.S. Pat. No. 4,049,657.

Pyrophosphates of lithium, sodium, strontium and barium have been used as dehydration catalysts; see U.S. Pat. No. 3,957,900. Phosphates and pyrophosphates of strontium and nickel have been used for the dehydrogenation of, for example, n-butene to butadiene under the conditions described in U.S. Pat. No. 3,541,172.

SUMMARY OF THE INVENTION

It has now been found that high yields of organic compounds are selectively obtained when the condensation reaction thereof is carried out in the presence of catalytic amounts of a catalyst selected from the group consisting of strontium pyrophosphate —$Sr_2P_2O_7$—, strontium dihydrogen phosphate —$Sr(H_2PO_4)_2$—, the pyrophosphate, monohydrogen phosphate and dihydrogen phosphate of copper, magnesium, calcium, barium, zinc, aluminum, lanthanum, cobalt, nickel, cerium and neodymium and mixtures thereof, and mixtures with strontium monohydrogen phosphate.

DETAILED DESCRIPTION OF THE INVENTION

The monohydrogen and dihydrogen phosphate catalysts of the present invention are prepared by reaction of a mono- or diphosphate of an alkali metal or ammonium with a soluble salt of strontium, copper, magnesium, calcium, barium, zinc, aluminum, lanthanum, cobalt, nickel, cerium or neodymium at ambient temperatures. The highest purity and best yields of the present invention are obtained when using the soluble metal salts of a strong acid such as the metal nitrates, in substantially stoichiometric proportion to the phosphate. In aqueous media under these conditions, the reaction mixture is at a pH of about 3.5 to 6.5. In general, to obtain a precipitate of desired high content of the metal monohydrogen or dihydrogen phosphate, the ratio of phosphate to metal salt in the reaction mixture should be such as to have a pH of $5\pm3$, or the mixture should be adjusted to that pH range.

The pyrophosphate form of the catalysts of the present invention are prepared by heat treating the metal monohydrogen or dihydrogen phosphate product at temperatures above about 300° C. up to 750° C. in the presence of a mixture of steam and air, preferably at least about 20% by volume of steam.

For use as a catalyst, the metal pyro-, monohydrogen or dihydrogen phosphate product may be employed in the form of irregular particles of the desired size range prepared by breaking up the washed and dried filter cake or in the form of regular shaped pellets obtained by known methods of casting or extruding or the product may be deposited or otherwise impregnated into the pores of a microporous substrate such as alumina, silica, silica-alumina, and the like. In using the catalyst of the present invention to catalyze organic condensation reactions, substantially the same conditions may be employed as when using the known catalysts for the particular synthesis. For optimum results, however, some adjustment in temperature, diluent and/or space rate may be found beneficial.

Some specific examples of the type of organic compounds selectively obtained by the method of this invention include TEDA, the aliphatic alkylamines such as methylamine, methylethylamine, dimethylethylamine, and dimethylaminoethylmorpholine. In the production of these compounds, the temperature is in the range of about 285° to 420° C., the pressure is in the range of about 0.1 to 1.5 atmospheres, and the liquid hourly space velocity (LHSV) of the organic feed stock per volume of catalyst is in the range of about 0.05 to 1.5. Preferably depending on the particular reaction, the temperature is in the range of about 340° to 400° C., the pressure is in the range of about 0.3 to 1.0 atmospheres and the LHSV is in the range of about 0.1 to 0.3 to obtain the highest yields and most economical process. The operable ratio of the organic feeds to water diluent is about 10 to 90% on a weight basis and preferably, 20 to 60% by weight. The optimum yield of these compounds is likely to be obtained using the highest temperature in the preferred range at the lowest LHSV.

In the preparation of TEDA, the preferred catalyst is selected from the group consisting of monohydrogen phosphate of calcium, magnesium, zinc, mixtures of strontium and barium in the ratio of Sr to Ba of about 1 to 5 to 5 to 1 and mixtures of lanthanum and strontium in the ratio of La to Sr of about 15 to 1 to 15. The organic feed stock used in this reaction to produce TEDA is a substituted piperazine compound selected from the group consisting of hydroxyethylpiperazine and aminoethylpiperazine. The catalysts of this invention are relatively uneffected by the purity of the feed stock. For example, high conversion and good yields can be obtained from crude hydroxyethylpiperazine which contains minor quantities of piperazine and bis hydroxyethylpiperazine.

In the preparation of dimethylaminoethylmorpholine (DMAEM), the preferred catalyst is a mixture of strontium and nickel monohydrogen phosphate in the ratio of Sr to Ni of about 1 to 5 to 5 to 1. The feed stock is morpholine and dimethylethanolamine in the molar ratio in the range of about 1 to 3 and 3 to 1. Preferably, the reaction takes place in the presence of hydrogen in the molar ratio of hydrogen to organic feed of about 1 to 1 to 20 to 1 and an inert gas such as nitrogen, argon or helium in the molar ratio of inert gas to organic feed of about 1 to 1 to 20 to 1.

The methods and catalysts of this invention are also capable of reacting an alcohol and a nitrogen-containing compound selected from the group consisting of ammonia, aliphatic primary and secondary amines, and aromatic primary and secondary amines to selectively convert this compound to the corresponding symmetrical or unsymmetrical higher molecular weight amine with little, if any, conversion to the corresponding by-products of thermodynamic amine equilibration. The amines and alcohol in the feed stock each contain 1 to 20 carbons per molecule. Preferably, the catalyst is lanthanum or copper monohydrogen phosphate and the molar ratio of alcohol to nitrogen-containing compound ranges from about 1 to 6 to 6 to 1.

CATALYST PREPARATION

EXAMPLE 1

195 grams of barium nitrate —$Ba(NO_3)_2$— and 53 grams of strontium nitrate —$Sr(NO_3)_2$— were dissolved in distilled water and diluted to 500 cc. 132 grams of dibasic ammonium phosphate —$(NH_4)_2HPO_4$— were dissolved in distilled water and diluted to 500 cc with heat. The three salt solutions were then combined with heat and stirred for about 10 minutes. The combined solution was vacuum filtered and the resulting precipitate was washed with distilled water and air dried overnight in a static oven at approximately 110° C. The filter cake was broken up into small ($\frac{1}{8}$ to $\frac{1}{4}$ inch) irregular granules for evaluation. The resulting product had a surface pH of 4-5 as determined by acid base indicators and the ratio of strontium to barium in the product was found to be 1/3.5.

EXAMPLE 2

The procedure for preparing the Example 1 was carried out except that 130 grams of $Ba(NO_3)_2$ and 106 grams of $Sr(NO_3)_2$ were dissolved in distilled water in place of the 195 and 53 grams respectively. The product had a surface pH of 4-5 and a Sr/Ba ratio of 2/1 mol/mol. The resulting catalyst was in the form of a fine powder and was deposited on an inert, low surface area Alundum silica-alumina core using a powder-coating step. The step comprised placing the amount of catalyst to be coated into a jar with the Alundum spheres and rotating on a jar-mill for several days to cause the catalyst powder to adhere to the spheres. The resulting coated spheres contained 25% of the active catalyst and 75% inert.

EXAMPLE 3

212 grams of $Sr(NO_3)_2$ were dissolved in distilled water and diluted to 500 cc. 115 grams of ammonium dihydrogen phosphate —$NH_4H_2PO_4$— were dissolved in distilled water and diluted to 500 cc. The remaining steps of the catalyst procedure of Example 1 were carried out. The resulting catalyst was believed to contain less than 5% strontium dihydrogen phosphate —$Sr(H_2PO_4)_2$— with the balance being $SrHPO_4$. The surface pH of this catalyst mixture was 4-4.6 in comparison to substantially pure strontium monohydrogen phosphate which has a surface pH of 4.8-5.4. Substantially pure strontium dihydrogen phosphate was found to have a surface pH of 0.2-1.2; see Example 19.

The product of this example was deposited on the silica-alumina spheres in the same manner as set forth under Example 2.

EXAMPLE 4

The same procedure for preparing the catalyst of Example 1 was carried out except that 236 grams of calcium nitrate —$Ca(NO_3)_2.4H_2O$— and 115 grams of $NH_4H_2PO_4$ were combined. The resulting dried catalyst particles were coated on the silica-alumina spheres in the same manner as that of Example 2. The analysis of the catalyst formed by this procedure indicated that it consisted essentially of calcium monodihydrogen phosphate with a Ca/P ratio of 1.009 and a surface pH of 4–6. In contrast, substantially pure calcium monohydrogen phosphate had a surface pH of 5–5.5; see Example 14 below. The presence of a very small amount of calcium dihydrogen phosphate may account for the difference in the surface pH value of this catalyst.

Control 1

The catalyst preparation procedure of Example 1 was repeated except that 212 grams of $Sr(NO_3)_2$ were dissolved in place of the mixed barium and strontium nitrate salts and the resulting strontium monohydrogen phosphate catalyst had a surface pH of 4.8–5.2.

EXAMPLES 5–13

The following salts were combined and catalysts were prepared in the manner set forth under Example 1:

| Example | Salt Solutions (a) | (b) | Catalyst Formulation | Surface pH |
|---|---|---|---|---|
| 5 | 168 g. $Nd(NO_3)_3.5H_2O$ | 80 g. $(NH_4)_2HPO_4$ | $Nd_2(HPO_4)_3$ | * |
| 6 | 217 g. $Ce(NO_3)_3.6H_2O$ | 99 g. $(NH_4)_2HPO_4$ | $Ce_2(HPO_4)_3$ | 0.2–1.2 |
| 7 | 415 g. $La(NO_3)_3.5H_2O$ | 198 g. $(NH_4)_2HPO_4$ | $La_2(HPO_4)_3$ | 0.2–1.8 |
| 8 | 202 g. $Sr(NO_3)_2$ + 20 grams of $La(NO_3)_3.5H_2O$ | 132 g. $(NH_4)_2HPO_4$ | $SrHPO_4/LaHPO_4$ (Sr/La = 14.9/1) | 4–5 |
| 9 | 291 g. $Co(NO_3)_2.6H_2O$ | 132 g. $(NH_4)_2HPO_4$ | $CoHPO_4$ | 4.6–4.8 |
| 10 | 291 g. $Ni(NO_3)_2.6H_2O$ | 132 g. $(NH_4)_2HPO_4$ | $NiHPO_4$ | 6.2–6.8 |
| 11 | 242 g. $CuCl_2.2.5H_2O$ | 132 g. $(NH_4)_2HPO_4$ | $CuHPO_4$ | * |
| 12 | 297 g. $Zn(NO_3)_2.6H_2O$ | 132 g. $(NH_4)_2HPO_4$ | $ZnHPO_4$ | 6.2–6.5 |
| 13 | 125 g. $Al(NO_3)_3.9H_2O$ | 66 g. $(NH_4)_2HPO_4$ | $Al_2(HPO_4)_3$ | 2 |

*Colored product, pH N.A.

EXAMPLE 14

160 grams of $Ca(NO_3)_4$ were dissolved in distilled water and diluted to 800 cc. 20 cc. of phosphoric acid (88% by wt. in water) were added with agitation. 34.5 cc. of sodium hydroxide solution (50% by wt. NaOH in water) were added to precipitate the $CaHPO_4$ which was filtered, washed, dried and granulated in Example 1. The resulting product had a surface pH of 5–5.5.

Controls 2–4

The following salts were also combined in the manner of the Example 1 preparation.

| Control | Salt Solutions (a) | (b) | Catalyst Formulation |
|---|---|---|---|
| 2 | 261 g. $Ba(NO_3)_2$ | 230 g. $NH_4HSO_4$ | $BaSO_4$ |
| 3 | 75 g. CsCl | 40 g. $(NH_4)_2HPO_4$ | $CsHPO_4$* |
| 4 | 106 g. $Sr(NO_3)_2$ | 40 g. 50% NaOH + 80 g. $(NH_4)_2H_2AsO_4$ | $SrHAsO_4$ |

*Did not form precipitate.

Control 5

200 grams of $Sr(NO_3)_2$ were dissolved in distilled water and diluted to 400 cc. 92 grams of $H_2SO_4$ were diluted in 200 cc. of distilled $H_2O$. 75 grams of 50 wt. % NaOH solution were diluted to 200 cc. with distilled water. The $H_2SO_4$ and NaOH solutions were mixed together slowly. The $Sr(NO_3)_2$ solution was stirred into the solution containing $H_2SO_4$ and NaOH. The solution was stirred for 10 minutes and the precipitate was filtered, washed and dried. The surface pH of the resulting catalyst was less than 3 which was believed to be substantially all $SrSO_4$.

EXAMPLE 15

71 grams of $Na_2HPO_4$ were dissolved in 500 cc. of distilled water. 101.7 grams of $MgCl_2.6H_2O$ were dissolved in 500 cc. of distilled $H_2O$. Both solutions were mixed together and the precipitate was filtered, washed and dried. The surface pH of the $MgHPO_4$ product was 7–8.

EXAMPLE 16

71 grams of $Na_2HPO_4$ and 130.7 grams of $Ba(NO_3)_2$ were each separately dissolved in 500 cc. of distilled $H_2O$. The 2 solutions were mixed and the precipitate was filtered, washed and dried. The resulting $BaHPO_4$ had a surface pH of 8–9.

Each of the products resulting from the procedures of Examples 15 and 16 above were coated on the silica-alumina spheres in the same manner as indicated in Example 2.

EXAMPLE 17

The $SrHPO_4$ catalyst of Control 1 was heat treated for 2 hours in the presence of a mixture 20% by volume steam and the balance air at 350° C. The resulting strontium pyrophosphate ($Sr_2P_2O_7$) had a crushing strength of 0.47 kg./mm of length and a packed bulk density of 1.01 kg./l.

EXAMPLE 18

The $ZnHPO_4$ catalyst product of Example 12 above coated on the silica-alumina spheres in the manner set forth in Example 2.

EXAMPLE 19

132.5 grams of strontium hydroxide octahydrate —$Sr(OH)_2.8H_2O$— were dissolved in a solution of 750 cc. of 85% phosphoric acid and 1500 cc. of distilled water. The resulting solution was slowly evaporated to a total volume of about 900 cc. with the temperature being maintained at 25° to 30° C. The solution was cooled to 5° C. overnight and a white precipitate was recovered by vacuum filtration. The resulting $Sr(H_2PO_4)_2$ precipitate was washed with 5–300 cc. portions of anhydrous ethanol and with 2–200 cc. portions of anhydrous ether. The product was dried at room temperature under vacuum for 6 hours. An elemental analysis of the product showed a P/Sr mol ratio of 2.04 and the surface pH was found to be 0.2–1.2. The fine powder was pressed into tablets the size of a typical aspirin tablet and crushed to granules ⅛ to ¼ inch in size.

EXAMPLE 20

The fine powder of the catalyst prepared in accordance with Example 19 was deposited on silica-alumina spheres in the manner set forth in Example 2.

EXAMPLE 21

106 grams of $Sr(NO_3)_2$ and 145 grams of $Ni(NO_3)_2.6H_2O$ were dissolved in distilled water and diluted to 500 cc. 132 grams of $(NH_4)_2HPO_4$ were dissolved in distilled water and diluted to 500 cc. the remaining steps of Example 1 were carried out to yield a $(Sr-Ni)HPO_4$ catalyst having a surface pH of 5.4–7.0.

USE OF CATALYSTS

EXAMPLES 22–54

Each of the products prepared in accordance with Examples 1 through 20 and Controls 1-2 and 4-6 above were evaluated for catalytic performance for the preparation of TEDA with either a feed mixture containing hydroxyethylpiperazine (HEP) or N-aminoethylpiperazine (AEP) in accordance with the following test procedure:

(a) 20 cc (approximately 6.2 g.) of the catalyst was loaded into a ¾" diameter stainless steel reactor.

(b) The reactor was placed in a conventional tube furnace such that the catalyst bed was near the furnace center and therefore could be heated to a constant and uniform temperature.

(c) The catalyst bed temperature was raised to a temperature of 340°–400° C. over a period of 15 to 30 minutes while a small flow of gaseous nitrogen was maintained through the reactor to aid in the removal of water vapor.

(d) A feed mixture containing HEP and water such that the organic component made up 60% of the mixture was then allowed to flow through the catalyst bed at a rate of 6.5–7.0 cc/hour; the nitrogen flow was discontinued.

(e) The catalyst bed temperature indicated in the tables set forth below was maintained during the run and the product samples were collected and analyzed. Analyses were performed using well-established gas chromatographic techniques.

The yields of TEDA and piperazine (PIP) as well as the conversion obtained from the catalysts of Examples 1–20 in Table 1 can be compared with those of Control Catalysts 1-2 and 4–6 in Table 2 below.

TABLE 1

TEDA PRODUCTION

| Example | Cat. of Ex. | Form | Nominal Formulation | TEDA Yield, Wt. % | PIP Yield, Wt. % | Conversion, Mol. % | Temp., °C. | Feed |
|---|---|---|---|---|---|---|---|---|
| 22 | 1 | Granules | $Sr/BaHPO_4$ (Sr/Ba = 1/3.5) | 83.8[1] | 7.0[2] | 99.9 | 360 | HEP |
| 23 | 2 | 25% Coated Spheres | $Sr/BaHPO_4$ (Sr/Ba = 2/1) | 67.8 | 5.5 | 99.1 | 380 | HEP |
| 24 | 2 | 25% Coated Spheres | $Sr/BaHPO_4$ (Sr/Ba = 2/1) | 13.8 | 9.1 | 56.8 | 400 | AEP |
| 25 | 3 | 25% Coated Spheres | $SrHPO_4/Sr(H_2PO_4)_2$ | 63.5 | 14.7 | 98.3 | 380 | HEP |
| 26 | 3 | 25% Coated Spheres | $SrHPO_4/Sr(H_2PO_4)_2$ | 18.8 | 16.4 | 77.0 | 400 | AEP |
| 27 | 4 | 25% Coated Spheres | $CaHPO_4/Ca(H_2PO_4)_2$ | 56.2 | 5.8 | 91.2 | 380 | HEP |
| 28 | 4 | 25% Coated Spheres | $CaHPO_4/Ca(H_2PO_4)_2$ | 34.4 | 9.9 | 90.2 | 380 | AEP |
| 29 | 5 | Granules | $Nd_2(HPO_4)_3$ | 18.2 | 5.4 | 98.4 | 340 | HEP |
| 30 | 5 | Granules | $Nd_2(HPO_4)_3$ | 7.5 | 2.1 | 92.6 | 360 | AEP |
| 31 | 6 | Granules | $Ce_2(HPO_4)_3$ | 32.3 | 8.4 | 99.9 | 340 | HEP |
| 32 | 6 | Granules | $Ce_2(HPO_4)_3$ | 7.8 | 7.9 | 92.6 | 360 | AEP |
| 33 | 7 | Granules | $La_2(HPO_4)_3$ | 16.2 | 4.2 | 98.8 | 340 | HEP |
| 34 | 7 | Granules | $La_2(HPO_4)_3$ | 25.5 | 3.3 | 95.2 | 380 | AEP |
| 35 | 8 | Granules | $La/SrHPO_4$ (La/Sr = 1/15) | 58.7 | 5.3 | 99.2 | 360 | HEP |
| 36 | 8 | Granules | $La/SrHPO_4$ (La/Sr = 1/15) | 27.4 | 14.6 | 96.1 | 380 | AEP |
| 37 | 9 | Granules | $CoHPO_4$ | 40.0 | 8.4 | 98.7 | 360 | HEP |
| 38 | 9 | Granules | $CoHPO_4$ | 19.4 | 17.4 | 91.9 | 380 | AEP |
| 39 | 10 | Granules | $NiHPO_4$ | 36.2 | 5.6 | 82.4 | 360 | HEP |
| 40 | 10 | Granules | $NiHPO_4$ | 6.0 | 7.8 | 56.7 | 380 | AEP |
| 41 | 11 | Granules | $CuHPO_4$[3] | 17.6 | 4.2 | 99.4 | 340 | HEP |
| 42 | 12 | Granules | $ZnHPO_4$ | 45.9 | 6.7 | 94.7 | 380 | HEP |
| 43 | 13 | Granules | $Al_2(HPO_4)_3$ | 39.7 | 9.4 | 98.3 | 380 | HEP |
| 44 | 13 | Granules | $Al_2(HPO_4)_3$ | 17.1 | 25.8 | 88.4 | 380 | AEP |
| 45 | 14 | Granules | $CaHPO_4$ | 59.2 | 23.5 | 99.6 | 360 | HEP |
| 46 | 15 | 25% Coated Spheres | $MgHPO_4$ | 47.2 | 15.8 | 99.9 | 380 | HEP |
| 47 | 16 | 25% Coated Spheres | $BaHPO_4$ | 23.2 | 1.0 | 37.4 | 380 | HEP |
| 48 | 17 | Granules | $Sr_2P_2O_7$ | 30.7 | 9.0 | 98.4 | 340 | HEP |
| 49 | 17 | Granules | $Sr_2P_2O_7$ | 41.0 | 9.0 | 99.2 | 360 | HEP |
| 50 | 18 | 25% Coated Spheres | $ZnHPO_4$ | 12.2 | 11.3 | 57.9 | 400 | AEP |
| 51 | 19 | Granules | $Sr(H_2PO_4)_2$ | 24.7 | 4.4 | 95.5 | 320 | HEP |
| 52 | 19 | Granules | $Sr(H_2PO_4)_2$ | 6.7 | 0.6 | 99.6 | 320 | AEP |
| 53 | 20 | 25% Coated Spheres | $Sr(H_2PO_4)_2$ | 22.0 | 3.6 | 98.9 | 320 | HEP |
| 54 | 20 | 25% Coated | $Sr(H_2PO_4)_2$ | 10.9 | 18.3 | 91.1 | 320 | AEP |

TABLE 1-continued
TEDA PRODUCTION

| Example | Cat. of Ex. | Form | Nominal Formulation | TEDA Yield, Wt. % | PIP Yield, Wt. % | Conversion, Mol. % | Temp., °C. | Feed |
|---|---|---|---|---|---|---|---|---|
| | | Spheres | | | | | | |

[1] 97.3 mol. % based on feed.
[2] 10.6 mol. % based on feed.
[3] Analysis of catalyst after reaction to produce TEDA indicated the formation of minor amounts of $CuP_2O_7$ and elemental Cu.

TABLE 2

| Catalyst of Control | Form | Nominal Formulation | TEDA Yield, Wt. % | PIP Yield, Wt. % | Conversion, Mol. % | Temp., °C. | Feed |
|---|---|---|---|---|---|---|---|
| 1 | Granules | $SrHPO_4$[6] | 76.0 | 7.8 | 98.6 | 360 | HEP |
| 1 | Granules | $SrHPO_4$ | 29.0 | 21.0 | 99.0 | 400 | AEP |
| 2 | Granules | $BaSO_4$ | 14.3 | 2.9 | 31.2 | 360 | HEP |
| 4 | 25% Coated Spheres | $SrHA_sO_4$ | 4.6 | 6.2 | 36.2 | 340 | HEP |
| 4 | 25% Coated Spheres | $SrHA_sO_4$ | 1.2 | 1.6 | 43.5 | 360 | AEP |
| 5 | Granules | $SrSO_4$ | 2.1 | 27.3 | 36.4 | 360 | HEP |
| 6[4] | Granules | $AlPO_4$ | 28.4 | 6.0 | 100 wt. % | 400 | HEP |
| 6[5] | Granules | $AlPO_4$ | 33.9 | 26.7 | 83 wt. % | 375 | AEP |

[4] Data obtained from Example II of U.S. Pat. No. 3,297,701.
[5] Data obtained from Example XXI of U.S. Pat. No. 3,297,701.
[6] Analysis of catalyst after reaction to produce TEDA indicates the formation of a minor amount of $SrP_2O_7$.

The results set forth in Table 1 where the catalysts of the examples demonstrate a unique ability to convert over 50 mol.% of the feed to products the majority of which is TEDA. Depending on the particular feed stock, the yield of TEDA ranged from 6% in the worst case using Ni to approximately 84% in the best mode using 1 part $SrHPO_4$ to 3.5 parts $BaHPO_4$, see Example 1 above. The former being the use of $NiHPO_4$ with an aminoethylpiperazine feed. When the feed over $NiHPO_4$ was changed to hydroxyethylpiperazine, the yield increased 6 fold with a corresponding increase in the conversion from approximately 57% to 82%. The $BaHPO_4$ catalysts per se did not meet the criteria for an effective catalyst for the conversion of HEP to TEDA. However, when approximately four parts of this catalyst were combined with one part of $SrHPO_4$ as in the Example 1, the yield of TEDA and the conversion increased based on a synergistic effect over that of the control catalyst, the use of which is disclosed and claimed in the parent application, Ser. No. 278,814.

EXAMPLE 55

The $CaHPO_4$ catalyst of Example 4 was recovered in a fine, powdered state and was deposited on inert alumina spheres instead of the silica-alumina spheres in the same manner as set forth under Example 2. 20 cc of the resulting coated alumina contained 2 gms. of $CaHPO_4$. The performance of this catalyst was evaluated for the preparation of an alipathic secondary amine with a feed mixture of monoethylamine (EA) and methanol using the general procedure used in Examples 22-54 for the preparation of TEDA. Specifically, 1 mol. of the primary amine and 1 mol. of the alcohol were reacted at 350° C., 1 atmosphere pressure and an LHSV of 0.15/hr. The conversion was 23.9 mol. % of the ME to the secondary aliphatic amine. The yield of methylethylamine (MEA) was 16.5 mol. % of the amine feed with a selectivity of 69 mol. %. The only other product in any significant quantity was dimethylethylamine (DMEA) with a yield of 5.4 mol. % and a selectivity of 22 mol. %.

EXAMPLE 56

The procedure of Example 55 was followed except that 1 mol. of diethylamine (DEA) was substituted for 1 mol of EA. 27.6 mol. % of this primary amine in the feed was converted for the most part to a single secondary amine, i.e. diethylmethylamine (DEMA) and a trace amount of a tertiary amine, i.e. triethylamine. The yield of DEA fed was 23 mol. % DEMA with a selectivity of 83.3 mol. %.

EXAMPLES 57-58

3 grams of the $La_2(HPO_4)_3$ catalyst of Example 7 were coated onto alumina spheres and the procedures of Example 55 and 56 were followed. The results from these reactions are summarized in Table 3 below.

Controls 7-8

The $SrHPO_4$ catalyst of Control 1, the use of which is disclosed and claimed in the parent application, was used to convert methanol and either monoethylamine (Control 7) or diethylamine (Control 8) in the same manner set forth under Example 55. The results of these control reactions are summarized and compared with those of Examples 55-58 in Table 3 below.

TABLE 3

| | Amine Feed | ALIPHATIC AMINE PRODUCTION | | | | | | Conversion Mol. % |
|---|---|---|---|---|---|---|---|---|
| | | Yield, mol. % | | | Selectivity, Mol. % | | | |
| | | MEA | DMEA[7] | DEMA | MEA | DMEA | DEMA | |
| Example | | | | | | | | |
| 55 | EA | 16.5 | 5.4 | — | 69 | 22 | — | 23.9 |
| 56 | DEA | — | — | 23 | — | — | 83.3 | 27.6 |
| 57 | EA | 27 | 25 | — | 47 | 44 | — | 57 |
| 58 | DEA | — | — | 39 | — | — | 66 | 59 |

TABLE 3-continued

| | Amine Feed | ALIPHATIC AMINE PRODUCTION | | | | | | Conversion Mol. % |
|---|---|---|---|---|---|---|---|---|
| | | Yield, mol. % | | | Selectivity, Mol. % | | | |
| | | MEA | DMEA[7] | DEMA | MEA | DMEA | DEMA | |
| Control | | | | | | | | |
| 7 | EA | 22 | 17 | — | 55 | 17 | — | 40 |
| 8 | DEA | 1.4 | 6.9 | 41 | 2.8 | 13.8 | 82 | 50 |

[7]Dimethylethylamine.

The data of Table 3 illustrates the unexpectedly high selectivities to the corresponding aliphatic amine without the formation of the corresponding by-products of thermodynamic amine equilibration. The relatively low conversion to product compared with the control can be attributed to the fact that only 2 gms. of $CaHPO_4$ or 3 gms. $La_2(HPO_4)_3$ were used in Examples 55–58 and about 20 gms. of $SrHPO_4$ were used in Controls 7 and 8.

EXAMPLE 59

The $CuHPO_4$ catalyst of Example 11 was coated onto alumina spheres and the procedure of Example 55 was followed except that 1 mol. of ammonia was substituted for 1 mol. of EA. The results from this reaction were a 65 mol. % yield of monomethylamine (MA) based on the methanol, an 87 mol.% selectivity to MA and an methanol conversion of 75 mol. %.

EXAMPLE 60

The $La_2(HPO_4)_3$ catalyst of Example 7 was deposited on alumina spheres and the procedure of Example 59 was followed. The results were yields based on the methanol in the feed of 13 mol. % trimethylamine (TMA), 2.8 mol. % dimethylamine (DMA) and 3 mol. % monomethylamine (MA), selectivities based on the methanol of 69 mol. % TMA, 14.9 mol. % DMA and 16 mol. % MA, and a methanol conversion of 52 mol. %.

It has also been found that $MgHPO_4$ and $BaHPO_4$ were effective in selectivity converting amines to the corresponding higher molecular weight amine.

EXAMPLES 61–67

The (Sr—Ni)$HPO_4$ catalyst of Example 21 was evaluated for the preparation of N-(2-dimethylaminoethyl)-morpholine (DMAEM) with a feed mixture of morpholine (MOR), dimethylethanolamine (DMEA), distilled water, hydrogen and helium in the amounts shown below in Table 4 using the general procedure used in Examples 22–54 for the TEDA preparation. Specifically the condensation reaction was carried out at 340° C., 1 atmosphere of pressure and an LHSV in the range of 0.31–0.44/hr. as shown in Table 4 in the presence of 20 cc. of the (Sr—Ni)$HPO_4$ catalyst granules.

Controls 9–12

The $SrHPO_4$ catalyst of Control 1 was used in place of the (Sr—NI)$HPO_4$ catalyst of Example 21 and the condensation reactions were carried out in the same manner as described under Examples 61–67. The results of these control runs are summarized and compared with the Examples 61–67 feed, yield and conversion data in Table 4 below.

TABLE 4

| | DMAEM PRODUCTION | | |
|---|---|---|---|
| Feed, Vol. % | LHSV, hr.$^{-1}$ | Yield, Mol. % MOR | Conversion, Mol. % |
| Example | | | |

TABLE 4-continued

| | DMAEM PRODUCTION | | |
|---|---|---|---|
| | Feed, Vol. % | LHSV, hr.$^{-1}$ | Yield, Mol. % MOR | Conversion, Mol. % |
| 61 | MOR 60 DMEA 20 H$_2$O 20 He (20 cc/min) H$_2$ (20 cc/min) | 0.31 | 100 | 16 |
| 62 | MOR 60 DMEA 20 H$_2$O 20 He (20 cc/min) H$_2$ (20 cc/min) | 0.44 | 63 | 23 |
| 63 | MOR 40 DMEA 40 H$_2$O 20 He (20 cc/min) H$_2$ (20 cc/min) | 0.31 | 53 | 43 |
| 64 | MOR 40 DMEA 40 H$_2$O 20 He (20 cc/min) H$_2$ (20 cc/min) | 0.21 | 58 | 48 |
| 65 | MOR 20 DMEA 60 H$_2$O 20 He (20 cc/min) H$_2$ (20 cc/min) | 0.31 | 52 | 60 |
| 66 | MOR 20 DMEA 60 H$_2$O 20 He (20 cc/min) H$_2$ (20 cc/min) | 0.21 | 58 | 75 |
| 67 | MOR 40 DMEA 40 H$_2$O 20 He (20 cc/min) H$_2$ (20 cc/min) | 0.31 | 97 | 21 |
| Control | | | | |
| 9 | MOR 40 DMEA 20 H$_2$O 20 He (20 cc/min) | 0.21 | 42 | 32 |
| 10 | MOR 40 DMEA 40 H$_2$O 20 He (20 cc/min) | 0.21 | 37 | 28 |
| 11 | MOR 60 DMEA 20 H$_2$O 20 He (20 cc/min) | 0.21 | 43 | 22 |
| 12 | MOR 20 DMEA 60 H$_2$O 20 He (20 cc/min) | 0.21 | 33 | 45 |

What is claimed is:

1. In methods for the synthesis of organic compounds by condensation reactions in the presence of phosphate catalysts, the improvement for producing triethylenediamine which comprises effecting condensation of an amine selected from the group consisting of hydroxyethyl piperazine, ethanolamine and N-aminoethylpiperazine in the presence of a catalyst comprising a mixture of a pyrophosphate, a monohydrogen phosphate or dihydrogen phosphate of strontium and a pyrophosphate, a monohydrogen phosphate or dihydrogen phosphate of barium.

2. The method as defined in claim 1 wherein such condensation reaction comprises the production of triethylenediamine from hydroxyethylpiperazine.

3. The method as defined in claimed 1 wherein such condensation reaction comprises the production of triethylenediamine from crude hydroxyethylpiperazine.

4. The method as defined in claim 1 wherein such reaction comprises the production of triethylenediamine from ethanolamines.

5. The method as defined in claim 1 wherein such condensation reaction comprises the production of triethylenediamine from N-aminoethylpiperazine.

6. The method as define in any of claims 1, 4, or 5 wherein the reaction is carried out in the presence of water.

7. A method which comprises converting a substituted piperazine compound selected from the group consisting of hydroxyethylpiperazine and aminoethylpiperazine to triethylenediamine at a temperature in the range of about 285° C. to 420° C., a liquid hourly space velocity of about 0.05 to 1.5 in the presence of a catalyst selected from the group consisting of the the pyrophosphate, monohydrogen phosphate and dihydrogen phosphate of barium, and strontium monohydrogen phosphate.

8. The method of claim 7 which comprises converting hydroxyethylpiperazine to greater than 50 mol.% yield of triethylenediamine at a temperature in the range of about 340° to 400° C., a liquid hourly space velocity of about 0.1 to 0.3 in the presence of a catalyst with a ratio of Sr to Ba of 1 to 5 to 5 to 1.

* * * * *